United States Patent [19]

Tamura et al.

[11] Patent Number: 5,354,745
[45] Date of Patent: Oct. 11, 1994

[54] ESTRADIOL DERIVATIVE-CHLORAMBUCIL CONJUGATE PROCESS FOR PREPARING THE SAME, AND PHARMACEUTICAL COMPOSITION

[75] Inventors: Fumio Tamura; Tsuyoshi Saito, both of Ibaraki; Satoshi Mitsuhashi; Tadahiro Matsudaira, both of Saitama; Kiro Asano, Ibaraki, all of Japan

[73] Assignee: Kureha Chemical Industry Co., Ltd., Tokyo, Japan

[21] Appl. No.: 70,797

[22] Filed: Jun. 3, 1993

[30] Foreign Application Priority Data

Jun. 11, 1992 [JP] Japan ............... 4-177363

[51] Int. Cl.$^5$ ............... C07J 1/00
[52] U.S. Cl. ............... 514/178; 514/179; 514/180; 514/182; 552/613; 552/614; 552/615; 552/617; 552/618; 552/626
[58] Field of Search ............... 552/613, 614, 615, 617, 552/618, 626; 514/182, 178, 179, 180

[56] References Cited

U.S. PATENT DOCUMENTS

| | | | |
|---|---|---|---|
| 4,261,910 | 4/1981 | Asano et al. | 424/238 |
| 4,332,797 | 6/1982 | Asano et al. | 424/238 |
| 4,885,290 | 12/1989 | Asano et al. | 514/182 |
| 4,921,849 | 5/1990 | Asano et al. | 514/182 |
| 4,938,897 | 7/1990 | Asano et al. | 514/169 |
| 5,036,062 | 7/1991 | Hansen et al. | 514/176 |

OTHER PUBLICATIONS

*Anticancer Research*, Kubota, et al., vol. 13 pp. 935–940 (1993).

Kosano, et al., *Cancer Research*, vol. 52, pp. 1187–1191 (1992).

*Primary Examiner*—Johann Richter
*Assistant Examiner*—Kimberly J. Kestler
*Attorney, Agent, or Firm*—Sughrue, Mion, Zinn, Macpeak & Seas

[57] ABSTRACT

An estradiol derivative-chlorambucil conjugate of the formula (I):

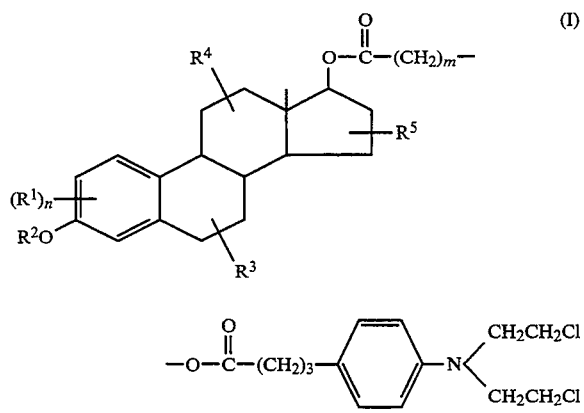

wherein $R^1$ is alkyl or alkoxyl of 1 to 4 carbon atoms; $R^2$ is acyl, dansyl, or alkyl; $R^3$, $R^4$, and $R^5$ independently are H, oxo, OH, or acyloxy; m is an integer of 1 to 3; and n is an integer of 0 to 3; provided that when n is 0, all of $R^3$, $R^4$, and $R^5$ are not H at the same time, and at least one of $R^3$, $R^4$, and $R^5$ is a group other than H and OH; and further, when n is 2 or 3, the groups $R^1$ are the same or different; a process for preparing the same, and a pharmaceutical composition containing the conjugate are described.

12 Claims, No Drawings

ESTRADIOL DERIVATIVE-CHLORAMBUCIL CONJUGATE PROCESS FOR PREPARING THE SAME, AND PHARMACEUTICAL COMPOSITION

BACKGROUND OF THE INVENTION

1. Field of the Invention

The present invention relates to a novel estradiol derivative-chlorambucil conjugate. More particularly, the present invention relates to a conjugate comprising a reaction product of an estradiol derivative and chlorambucil, a process for preparing the same, and a pharmaceutical composition comprising the conjugate.

2. Description of the Related Art

There are many conventional antitumor agents which inherently have strong antitumor effects, but in fact do not sufficiently exhibit their inherent effects. The main reason is that the amount of administration is limited due to their side effects. One of the attempts to solve the above problem is to bind the antitumor agent with a carrier having specific affinity to the tumor sites, and thereby form a conjugate of an antitumor agent and a carrier. The attempt intended to accumulate the antitumor agent specifically to the tumor sites and effectively exhibit the antitumor effect while reducing the side effects.

On the basis of the above conception, an estradiol-chlorambucil conjugate and an antitumor agent containing mainly the conjugate were already proposed in U.S. Pat. No. 4,261,910 and U.S. Pat. No. 4,332,797. The antitumor agent can accumulate specifically to the tumor sites and exhibit a strong antitumor effect thereat. Further, its influence on normal cells is extremely small.

Recently, H. Kosano, et al. reported that the above estradiol-chlorambucil conjugate inhibits the estrogen effect to promote the growth of MCF-7 (human breast carcinoma cell, its growth is promoted by estrogen), irreversibly or over an extremely long period (Hiroshi Kosano, et al., Cancer Research 52, 1187–1191, 1992). The reason thereof is suggested that the decrease in estrogen receptors causes a loss of the estrogen sensitivity of the cell, followed by inhibition of transforming growth factor (TGF)-$\alpha$ secretion and succeeding inhibition of the cell growth. It is also suggested that the structure of the conjugate is necessary for the conjugate to exhibit the above effects on the estrogen receptors and inhibit the secretion of TGF-$\alpha$. That is, it is not suggested that the above effects are caused by chlorambucil liberated in the process of the conjugate degradation.

Further, U.S. Pat. No. 4,921,849 discloses an injection prepared by dissolving the above estradiol-chlorambucil conjugate in an ester of iodinated poppy oil fatty acid. The injection enables the conjugate to reside for a long period at the tumor sites and to exhibit its full pharmacological effects. Further, U.S. Pat. No. 4,885,290 discloses an immunoregulator containing as an active ingredient the above conjugate which selectively suppresses immunoreactions caused specifically by isoantigen. Thus, the estradiol-chlorambucil conjugate exhibits selective physiological activities, such as a selective antitumor effect, a selective immunosuppressive effect and the like.

When an antitumor agent is administered for a long period, however, even weak side effects, which do not pose a problem with short term administration, in fact accumulate and become significant problems. In particular, a cancer patient lacks vital force, and therefore, such an accumulation of weak side effects is intensified. One of the problems with the conjugate is an adverse effect by a slight amount of estrogen released in the body from the estradiol-chlorambucil conjugate. For example, with long term administration of the conjugate, the slight amount of the released estrogen accumulates and may cause side effects such as gynecomastia, mastosis, nipple pain, genital bleeding, and the like. These estrogenic activities may be a problem even in the injections, immunoregulator or the like containing the above conjugate.

SUMMARY OF THE INVENTION

The present inventors discovered that an extremely useful, improved novel estradiol derivative-chlorambucil conjugate with no or reduced estrogenic activity can be obtained by introducing one or more particular substituents into one or more estradiol rings, while maintaining the selective physiological activities of the conventional estradiol-chlorambucil conjugate, that is, the selective antitumor effect and selective immunosuppressive effect.

Therefore, an object of the present invention is to provide a novel estradiol derivative-chlorambucil conjugate.

Another object of the present invention is to provide a process for preparing the estradiol derivative-chlorambucil conjugate.

A still another object of the present invention is to provide a pharmaceutical composition comprising the estradiol derivative-chlorambucil conjugate.

Other objects and effects of the present invention will be apparent from the following description.

According to the present invention, there is provided an estradiol derivative-chlorambucil conjugate of the formula (I):

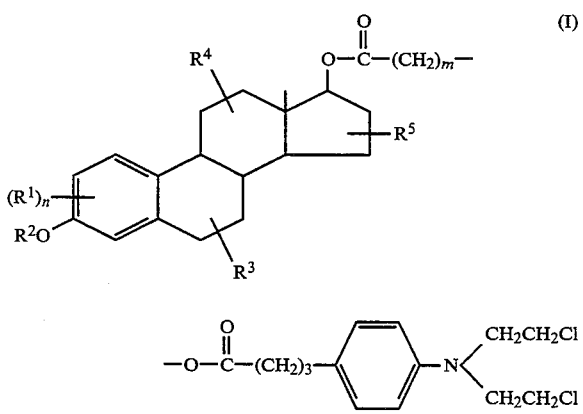

wherein $R^1$ is alkyl or alkoxyl of 1 to 4 carbon atoms; $R^2$ is acyl, dansyl, or alkyl; $R^3$, $R^4$, and $R^5$ independently are H, oxo, OH, or acyloxy; m is an integer of 1 to 3; and n is an integer of 0 to 3; provided that when n is 0, all of $R^3$, $R^4$, and $R^5$ are not H at the same time, and at least one of $R^3$, $R^4$, and $R^5$ is a group other than H and OH; and further, when n is 2 or 3, the groups $R^1$ are the same or different.

Further, according to the present invention, there are provided a process for preparing the above estradiol derivative-chlorambucil conjugate and a pharmaceutical composition comprising the estradiol derivative-chlorambucil conjugate.

Still further, according to the present invention, there is provided an intermediate of the above estradiol derivative-chlorambucil conjugate, namely an estradiol derivative of the formula (III):

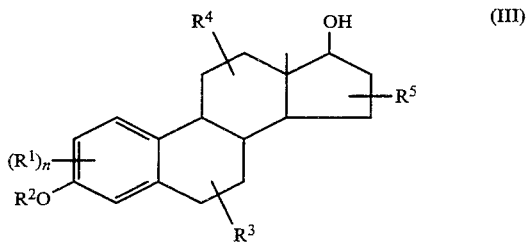

wherein $R^1$, $R^2$, $R^3$, $R^4$, $R^5$, and n have the same meanings as above.

Still further, according to the present invention, there is also provided another intermediate of the above estradiol derivative-chlorambucil conjugate, namely a compound of the formula (II):

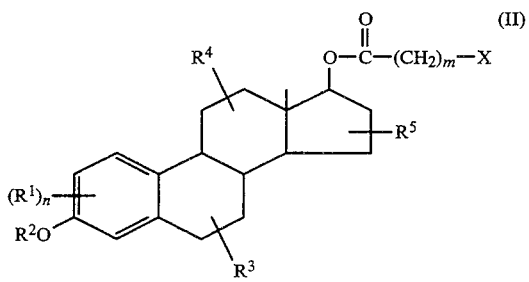

wherein $R^1$, $R^2$, $R^3$, $R^4$, $R^5$, m, and n have the same meanings as above, and X is halogen, OH, or a salt thereof.

DETAILED DESCRIPTION OF THE PREFERRED EMBODIMENTS

The estradiol derivative-chlorambucil conjugate of the present invention (hereinafter referred to as the present conjugate) contains an estradiol derivative moiety characterized by the chemical structures as follows:

That is, in addition to $OR^2$ at the 3-position on the ring A of the estradiol, the estradiol derivative moiety has one or more substituents at the 1-, 2-, and/or 4-position of the ring A, or at one or more positions on the rings B, C, and/or D. The estrogenic action can be eliminated or reduced by at least one substituent at $R^1$ (one or more) on the ring A, $R^3$ (other than H) on the ring B, $R^4$ (other than H) on the ring C or $R^5$ (other than H) on the ring D, but preferably one or more groups $R^1$ at the 1-, 2-, and/or 4-position on the ring A. $R^1$ at the 1-, 2-, and/or 4-position on the ring A may be alkyl of 1 to 4 carbon atoms or alkoxyl of 1 to 4 carbon atoms. $R^1$ is preferably present at the 1- and/or 4-position. Further, the estradiol derivative moiety may carry one of oxo, OH, and acyloxy on one of the rings B, C, and D, or each of same or different two or three substituents on two or three different rings of the rings B, C, and/or D. In this case, oxo or acyloxy is preferable. The acyloxy is preferably acyloxy of 2 to 7 carbon atoms, for example, benzoyloxy, acetoxy, propanoyloxy, butanoyloxy, or pentanoyloxy group.

The substituent at the 3-position of the estradiol derivative moiety in the present conjugate has a structure wherein H of OH at the 3-position of the estradiol is substituted by acyl, dansyl (5-dimethyleuninonaphthalenesulfonyl), or alkyl. $R^2$ as acyl is preferably acyl of 2 to 18 carbon atoms, for example, benzoyl, acetyl, palmitoyl, stearoyl, or linolenoyl. Further, $R^2$ as alkyl is preferably alkyl of 1 to 4 carbon atoms, more preferably methyl, ethyl, or propyl. Further, the configuration of OH at the 17-position of the estradiol derivative moiety may be β-configuration, α-configuration, or a mixture thereof, but β-configuration is preferable. The configuration of each of the substituents $R^3$, $R^4$, and $R^5$ may also be β-configuration, α-configuration, or a mixture thereof.

The present conjugate may be prepared, for example, by the following method:

When an estradiol derivative having OH at the 3-position on the ring A of the estradiol and the 17-position on the ring D of the estradiol (that is, an estradiol derivative having $R^1$ at the 1-, 2-, or 4-position on the ring A and/or having $R^3$, $R^4$, and/or $R^5$ other than H on the ring B, C, and/or D: hereinafter referred to simply as a "3,17-OH estradiol derivative") is used and H of OH at the 3-hydroxyl group is replaced by an acyl or dansyl group $R^2$, the 3,17-OH estradiol derivative is first dissolved in an organic solvent, and then reacted with an alkaline metal or an alkaline metal hydroxide to form a salt. Then, the salt is reacted with an acid chloride or acid anhydride corresponding to the desired acyl or dansyl group. Alternatively, an alkaline metal hydroxide is first dissolved in a mixture of acetone and water, and then the 3,17-OH estradiol derivative is added thereto. Thereafter, the resulting salt is reacted with an acid chloride or acid anhydride corresponding to the desired acyl or dansyl group. When $R^2$ is dansyl, dansyl chloride (5-dimethylamino-1-naphthalenesulfonyl chloride) is used as the acid chloride.

When H of the 3-hydroxyl group in the 3,17-OH estradiol derivative is substituted with the alkyl group $R^2$, it is possible to apply a usual alkyletherification method. For example, a dialkyl sulfate such as dimethyl sulfate and a dilute alkaline solution are reacted with the 3,17-OH estradiol derivative.

Accordingly, an estradiol derivative carrying the $OR^2$ group at the 3-position on the ring A, i.e., a compound (hereinafter referred to as a "3-$OR^2$ estradiol derivative") of the formula (III):

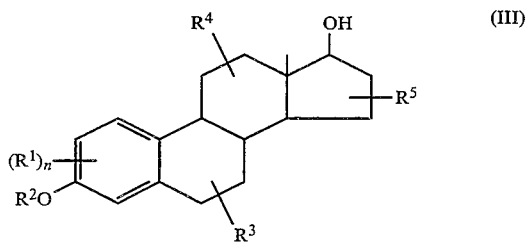

wherein $R^1$, $R^2$, $R^3$, $R^4$, $R^5$, and n have the same meanings as above, is obtained.

A binding agent may be used to couple the 3-$OR^2$ estradiol derivative and chlorambucil. The binding agent may be a hydroxylated or halogenated carboxylic acid derivative of the formula (IV):

$$X(CH_2)_mCOY \qquad (IV)$$

wherein X is halogen (for example, chlorine or bromine) or OH; Y is halogen which is the same as or different from X (for example, chlorine or bromine), OH, or a salt thereof; and m is an integer of 1 to 3. As examples of such carboxylic acid derivatives, there may be mentioned monochloroacetic acid, monobromoacetic acid, β-monochloropropionic acid, β-monobromopropionic acid, monochloroacetyl chloride, and monobromoacetyl bromide.

It is possible to react the 3-OR$^2$ estradiol derivative and the binding agent to esterify the 17-hydroxyl group and obtain the compound of the formula (II):

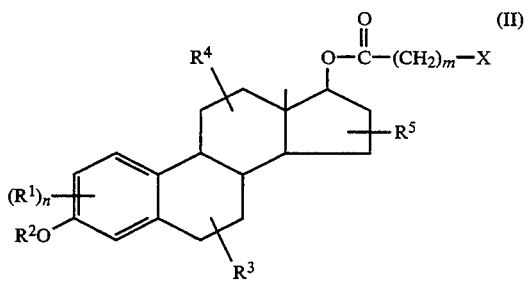

wherein $R^1$, $R^2$, $R^3$, $R^4$, $R^5$, m, n, and X have the same meanings as the above. The resulting compound will be hereinafter referred to as the "compound (II)". The reaction may be performed in an organic solvent, for example, dimethyl sulfoxide, dimethylformamide, pyridine, acetone, or tetrahydrofuran at $-10°$ to $+30°$ C.

Then, the compound (II) is reacted with chlorambucil. The carboxylic acid moiety of chlorambucil may be a salt with a metal (for example, sodium, potassium, silver, or calcium), an acid halide or an acid anhydride and further the chlorambucil derivatives may be a hydrochloride thereof. The reaction may be performed in an organic solvent, for example, dimethyl sulfoxide, dimethylformamide, pyridine, benzene, acetone, toluene, carbon tetrachloride, chloroform, or tetrahydrofuran. An aqueous alkaline solution may be added, if necessary. The reaction may be performed at $-30°$ to $+150°$ C., preferably 0° to 100° C., for 0.1 to 90 hours, preferably 0.5 to 75 hours. The reaction product may be purified by a suitable method to obtain the present conjugate. As the purification method, there may be used extraction, chromatography, crystallization, reprecipitation, etc.

The order of the above reaction steps may be changed, if appropriate. Examples of the changes are as follows:

(1) The chlorambucil and the binding agent are first reacted, and then the 3-OR$^2$ estradiol derivative is coupled thereto.

(2) After the coupling of the chlorambucil and 3,17-OH estradiol derivative via the binding agent, H of the 3-hydroxyl group of the estradiol derivative moiety may be substituted.

(3) In cases where one or more acyloxy groups are introduced onto the ring B, C, and/or D, one or more hydroxyl groups are introduced to the desired position(s) on the ring B, C, and/or D, and then esterification thereof is performed.

The structures of the present conjugate thus obtained may be confirmed by IR (infrared) spectrum, UV (ultraviolet) spectrum, NMR (nuclear magnetic resonance), elementary analysis, mass spectrum, etc.

The toxicity and pharmacological activities of the present conjugate are as follows:

(1) Toxicity

Each of 18 types of the present conjugates was orally administered to Wistar rats in an amount of 5000 mg/kg. No death was observed over a period of one week. Therefore, the present conjugate is extremely safe. See Example 3.

(2) Estrogen effects (measurement of uterus weight)

The estrogen effects of 18 types of the present conjugates were investigated. No or only slight estrogen effect was observed. See Example 4.

(3) Selective antitumor effect

In the following experiments (a) to (f), the present conjugate exhibited a selective antitumor effect comparable or superior to that of the comparative substance (estradiol-chlorambucil conjugate).

(a) Selective growth inhibitory effect for transformed mouse cells

The present conjugate considerably lowered the survival rate of transformed mouse cells (3T3SV-40), whereas it did not affect the survival rate of normal mouse cells (3T3). See Example 5(1).

(b) Selective growth inhibitory effect for human cancer cells

The present conjugate considerably lowered the survival rate of various types of human cancer cells [human renal cancer (RC) cells, human prostatic carcinoma (PC-3) cells, human cervical cancer (HeLa) cells], whereas it did not affect the survival rate of normal human cells (FLOW4000). See Example 5(2).

(c) Effect for secretion of transforming growth factor (TGF)-α from human breast carcinoma cells (MCF-7)

The present conjugate inhibited the secretion of TGF-α induced by the estradiol. This shows that the present conjugate has the effect of killing cancer cells while inhibiting the secretion of the cancer transforming growth factor. See Example 6.

(d) Antitumor effect (intraperitoneal and oral administration)

The present conjugate exhibited a life-prolonging effect (macrobiotic effect) on cancer-bearing BDF$_1$ female mice into which P388 cells had been transplanted intraperitoneally. See Example 7.

(e) Antitumor effect (intra-arterial administration of injection)

The present conjugate exhibited a macrobiotic effect on rat tumor Walker 256. See Example 8.

(f) Selective accumulation into cancer tissue transplanted in the liver and estrogen effect by liver intra-arterial administration The concentration of the present conjugate in cancer tissue transplanted in the liver was higher than the concentration in normal liver tissue. The present conjugate did not enlarge the uterus. See Example 9.

(4) Selective immunosuppressive effect

In the following experiments (a) to (d), the present conjugate exhibited a selective immunosuppressive effect comparable to that of the comparative substance (estradiol-chlorambucil conjugate).

(a) Heteroantigen stimulating reaction

The present conjugate did not considerably affect the blastogenesis reaction of the lymphocytes on phytohemagglutinin (HA). See Example 10(1).

(b) Isoantigen stimulating reaction

The present conjugate inhibited the mixed lymphocyte culture (MLC) reaction. See Example 10(2).

(c) Activity to inhibit GVHR (graft versus host reaction) in a mouse bone marrow transplant model The present conjugate increased the survival days of the mice after the transplant. See Example 11.

(d) Relation to TGF-$\beta$ in MLC reaction

The present conjugate exhibited a combined effect with the immunosuppressive substance (TGF-$\beta$). The inhibitory effect of the present conjugate was neutralized by the anti-TGF-$\beta$ antibodies. Therefore, it is considered that mechanism of inhibitory effect by the present conjugate relates to TGF-$\beta$ in the MLC reaction. See Example 12.

As above, the present conjugate has selective physiological activities, that is, a selective antitumor or immunosuppressive effect, and so is useful as a pharmaceutical composition, in particular an antitumor agent or an immunosuppressive agent. As the antitumor agent, it is effective against carcinomas in, for example, the breast, ovary, uterus, stomach, rectum, colon, kidney, hematopoietic system, liver or urinary organs, or other solid tumors.

When the present conjugate is used as an antitumor agent, various pharmaceutical compositions suitable for administering via various routes may be formulated by any conventional methods. As examples of the formulations, there may be mentioned oral agents such as capsules, syrups, pills or tablets, injections, external agents, and suppositories. As examples of the external agents, there may be mentioned a solid agent containing a usual base such as white vaseline and a penetration enhancer such as N,N-diethanol lauramide.

The present conjugate as an antitumor agent has a characteristic feature that a cross tolerance with the existing medicaments is slight.

The pharmaceutical composition may contain the present conjugate in an amount of preferably 0.01 to 75% by weight, more preferably 0.05 to 25% by weight. The present conjugate may be administered orally, transdermally, intramuscularly, intravenously, intra-arterially, intrarectally, etc. The dosage varies with the administration method and the degree of treatment, but generally is as follows: for an adult, the dosage of oral administration is 0.1 no 50 mg/kg per day, while the dosage of parenteral administration is 0.01 to 20 mg/kg per day.

When the present conjugate is contained in an injection for intra-arterial administration (i.e., an intra-arterial injection), it is preferable to dissolve the present conjugate in an ester of iodinated poppy oil fatty acid. The concentration of the present conjugate in the intra-arterial injection is preferably 0.1 to 10% by weight, more preferably 1 to 5% by weight. As the ester of iodinated poppy oil fatty acid, a lower alkyl ester wherein an iodination degree is 30 to 40% by weight is preferable. Lipiodol (trade name of Lipiodol Ultra-Fluide) (iodination degree of 38.8% by weight; ethyl ester) is more preferable. The dosage of the intra-arterial injection is preferably 0.01 to 20 mg/kg, more preferably 0.1 to 10 mg/kg. The intra-arterial injection is effective against a carcinoma in the liver, breast, gynecologic organs, gastrointestinal organs, and urogenital organs. The intra-arterial injection accumulates specifically in carcinoma tissue and stays there for a long period. Further, the use of an ester of iodinated poppy oil fatty acid makes it possible to perform diagnosis or medical treatment while observing the tumor cells by X-rays, CT (computer tomography), ultrasonic waves, etc.

The present conjugate is effective as an immunosuppressive agent in the organ transplantation, for example, for the prevention and treatment of rejection reactions in the transplantation of the kidney, liver, heart, skin, bone marrow, or the like, and further for the treatment of autoimmune diseases such as various types of renal diseases, thyroid diseases, chronic articular rheumatism, aplastic anemia, systemic lupus erythematosus, myasthenia gravis, liver diseases, polyarteritis, and dermatomyositis. Therefore, the present conjugate may be used as a preventing or treating agent for rejection in the organ transplantation, and a treating agent for autoimmune diseases.

When the present conjugate is used as an immunosuppressive agent, various pharmaceutical compositions suitable for administering via various routes may be formulated by conventional methods. As examples of the formulation, there may be mentioned oral agents such as tablets, granules, dispersions or capsules, suppositories, injections or external agents. The administration routes and dosages are the same as in the antitumor agents mentioned above.

As above, the estradiol derivative moiety in the present conjugate carries one or more substituents in addition to the 3-substituent present also in the conventionally known estradiol derivative moiety. By virtue of such a structure, it is possible to eliminate or tremendously weaken the estrogen effect of the conventionally known conjugate, while maintaining the selective physiological activities of the conventional estradiol-chlorambucil conjugate, namely, the selective antitumor effect and the selective immunosuppressive effect. Therefore, the usefulness as an antitumor or immunosuppressive agent is remarkably increased.

EXAMPLES

The present invention now will be further illustrated by, but is by no means limited to, the following examples.

In the following examples, the physical properties of the compound were measured by the following methods:

(1) Thin layer chromatography (silica gel): Silica gel thin layer plate LK6DF (layer thickness=250 ram; Whatman Co.)
(2) Elementary analysis: Yanaco CHN-CORDER MT-3 (Yanagimoto Co.)
(3) Mass spectrum: Mass spectrometer JMS-DX303 (JOEL)
(4) NMR (CDCl$_3$): JNM-GSX-500 (JOEL)
(5) Fluorometric analysis: Shimadzu Spectrophotoflucrometer RF-540 ( Shimadzu Co.)

Example 1

[1] Preparation of
1-methyl-estra-1,3,5(10)-triene-3,17$\beta$-diol, 3-benzoate, 17-monobromoacetate Acetone (200 ml) and 1-methyl-estra-1,3,5 ( 10 ) -triene-3,17$\beta$-diol (7.2 g) were placed in a four-neck flask (500 ml), agitated to dissolve them, and then 1N-NaOH (0.028 mole as NaOH) was added thereto. A solution of benzoyl chloride (4.2 g) in acetone (20 ml) was added dropwise to the solution while cooling with ice. A viscous substance was precipitated. Thus, the viscous substance was extracted with chloroform (200 ml + 100 ml)

and the organic layers were washed with water, then treated with magnesium sulfate, and dried under reduced pressure to obtain a light yellow viscous substance (9.9 g). The $\nu_{C=O}$ absorption was confirmed in IR spectrum of the substance. The product was developed by thin layer chromatography (silica gel; developing solvent: cyclohexane/ethyl acetate (5/2; v/v)), whereupon an Rf of the product was 0.27 and the disappearance of the raw material spot (Rf=0.18) was confirmed.

Then, the resulting 1-methyl-estra-1,3,5(10)-triene-3,17$\beta$-diol, 3-benzoate (9.9 g), dry tetrahydrofuran (250 ml) and pyridine (2.4 g) were placed in a four-neck flask (500 ml) equipped with a calcium chloride tube, then a solution of bromoacetyl bromide (10 g) in dry tetrahydrofuran (80 ml) was added dropwise at $-5°$ C. to $-3°$ C. The mixture was agitated at 0° C. for 1 hour. After the disappearance of the raw material had been confirmed by thin layer chromatography, the precipitated pyridine-HBr salt was filtered out and the filtrate was dried under reduced pressure. The residue was purified by silica gel column chromatography [developing solvent: chloroform/n-hexane (2/1; v/v)] to obtain the title compound (9.3 g). The physicochemical data was as follows:

Rf: 0.70 [cyclohexane/ethyl acetate (5/2; v/v) ]
Elementary analysis for $C_{28}H_{31}O_4Br$:
  Calculated (%): C: 65.77, H:6.06, Br:15.64
  Found (%): C:66.0, H:6.1, Br:15.9
EI-MS: m/z 510 (parent ion peak)

The intermediate products shown in Table 1 were prepared by a similar method.

TABLE 1

| No. | Intermediates | Rf[1] | m/z[2] |
|---|---|---|---|
| 1 | 4-methyl-estra-1,3,5(10)-triene-3,17$\beta$-diol,3-benzoate,17-monobromoacetate | 0.70 | 510 |
| 2 | 2-methyl-estra-1,3,5(10)-triene-3,17$\beta$-diol,3-benzoate,17-monobromoacetate | 0.71 | 510 |
| 3 | 2-ethyl-estra-1,3,5(10)-triene-3,17$\beta$-diol,3-benzoate,17-monobromoacetate | 0.81 | 524 |
| 4 | 2-isopropyl-estra-1,3,5(10)-triene-3,17$\beta$-diol,3-benzoate,17-monobromoacetate | 0.88 | 538 |
| 5 | 1,2-dimethyl-estra-1,3,5(10)-triene-3,17$\beta$-diol,3-benzoate,17-monobromoacetate | 0.80 | 524 |
| 6 | 1,4-dimethyl-estra-1,3,5(10)-triene-3,17$\beta$-diol,3-benzoate,17-monobromoacetate | 0.79 | 524 |
| 7 | 2-methoxy-1-methyl-estra-1,3,5(10)-triene-3,17$\beta$-diol,3-benzoate,17-monobromoacetate | 0.79 | 549 |
| 8 | 2-methoxy-estra-1,3,5(10)-triene-3,17$\beta$-diol,3-benzoate,17-monobromoacetate | 0.69 | 535 |
| 9 | 1-methyl-estra-1,3,5(10)-triene-3,17$\beta$-diol,3-benzoate,17-($\beta$-monobromopropionate) | 0.80 | 524 |
| 10 | 1-methyl-estra-1,3,5(10)-triene-3,17$\beta$-diol,3-benzoate,17-($\gamma$-monobromobutyrate) | 0.85 | 538 |

[1]Mobility in silica gel thin layer chromatography Silica gel LK6DF (Whatman Co.) Developing solvent: Cyclohexane/ethyl acetate (5/2; v/v)
[2]Parent ion peak in mass spectrum (EI)

[2] Preparation of 1-methyl-estra-1,3,5(10)-triene-3,17$\beta$-diol, 3-(5-dimethylaminonaphthalenesulfonate), 17-monobromoacetate Acetone (100 ml) and 1-methyl-estra-1,3,5 (10)-triene-3,17$\beta$-diol (9 g) were placed in a four-neck flask (2000 ml) and agitated to dissolve. NaOH (1N; 32.5 ml) was added, and then a solution of 5-dimethylaminonaphthalenesulfonyl chloride (dansyl chloride: DNS-Cl) (9.2 g) in dry acetone (200 ml) was added dropwise thereto at 10° to 15° C. The mixture was agitated for 3 hours. After the end of the reaction had been confirmed by thin layer chromatography (silica gel; developing solvent: cyclohexane/ethyl acetate (5/2; v/v)), the acetone was removed under reduced pressure, and then the residue was extracted with chloroform (200 ml$\times$3). The chloroform layers were collected, dried over magnesium sulfate, and then further dried under reduced pressure to obtain a yellow viscous substance (31.3 g). Column chromatography using silica gel [cyclohexane/ethyl acetate (5/2; v/v)] was carried out to obtain 1-methyl-estra-1,3,5(10)-triene-3,17$\beta$-diol,3-(5-dimethylaminonaphthalenesulfonate) (12 g).

Rf: 0.15 [cyclohexane/ethyl acetate (5/2; v/v)]
Elementary analysis for $C_{31}H_{37}NO_4S$:
  Calculated (%): C: 71.64, H:7.18, N:2.70
  Found (%): C:71.5, H:7.2, N:2.6
EI -MS: m/z 519 (parent ion peak)
Fluorometric analysis:
  Excitation: 356 nm
  Emission: 520 nm Then, the resulting 1-methyl-estra-1,3,5(10)-triene-3,17$\beta$-diol, 3-(5-dimethylaminonaphthalenesulfonate) (12 g) , dry tetrahydrofuran (200 ml), and pyridine (5 g) were placed in a four-neck flask (500 ml) equipped with a calcium chloride tube and agitated at $-5°$ C. to $-3°$ C. A solution of bromoacetyl bromide (7.6 g) in dry tetrahydrofuran (40 ml) was added dropwise to the solution. The mixture was agitated at 0° C. for 1 hour, and further agitated at room temperature overnight. After the disappearance of the raw material had been confirmed by thin layer chromatography, the precipitated pyridine-HBr salt was filtered out, and then the filtrate was treated with magnesium sulfate. The solvent was removed under reduced pressure to obtain a yellow-white solid. The solid was purified by column chromatography using silica gel [cyclohexane/ethyl acetate ( 5/2; v/v)] to obtain the title compound.

Rf: 0.62 [cyclohexane/ethyl acetate ( 5/2; v/v) ]
Elementary analysis for $C_{33}H_{38}NO_5SBr$:
  Calculated (%): C:61.87, H:5.98, Br:12.47, N:2.19
  Found (%): C:61.7, H:5.8, Br:13.0, N:2.2
$^1$H-NMR (CDCl$_3$): $\delta$
  2.90 ppm (S, CH$_3$, DNS-N (CH$_3$)$_2$)
  2.14 ppm (S, CH$_3$, Ar-CH$_3$)
  0.70 ppm (S, CH$_3$, E$_2$-18CH$_3$)
EI-MS: m/z 639 (parent ion peak)
Fluorometric analysis:
  Excitation: 355 nm
  Emission: 525 nm
Flame reaction: Halogen coloration In the same manner as mentioned above, the intermediates shown in the following Table 2 were prepared.

TABLE 2

| No. | Intermediates | $R_f$ | m/z(3) |
|---|---|---|---|
| 1 | 1-methyl-estra-1,3,5(10)- | 0.85(1) | 490 |

TABLE 2-continued

| No. | Intermediates | $R_f$ | m/z(3) |
|---|---|---|---|
| 2 | triene-3,17$\beta$-diol,3-acetate,17-monobromoacetate 1-methyl-estra-1,3,5(10)-triene-3,17$\beta$-diol,3-palmitate,17-monobromoacetate | 0.70(2) | 644 |
| 3 | 1-methyl-estra-1,3,5(10)-triene-3,17$\beta$-diol,3-stearate,17-monobromoacetate | 0.80(2) | 672 |
| 4 | 1-methyl-estra-1,3,5(10)-triene-3,17$\beta$-diol,3-linolenate,17-monobromoacetate | 0.92(2) | 666 |

(1)Mobility of silica gel thin layer chromatography Silica gel LK6DF (Whatman Co.) Developing solvent: Cyclohexane/ethyl acetate (5/2; v/v)
(2)Mobility of silica gel thin layer chromatography Silica gel LK6DF Developing solvent: Chloroform/ethyl acetate (50/1; v/v)
(3)Parent ion peak in mass spectrum (EI)

[3] Preparation of estra-1,3,5(10)-triene-3,16$\alpha$,17$\beta$-triol,3-benzoate,17-monobromoacetate An eggplant type flask (300 ml) was charged with estriol (5 g), acetone (45 ml), distilled water (150 ml), and 1N-NaOH (20.6 ml). The mixture was agitated to dissolve. The solution was cooled to 0° C., then a solution of benzoyl chloride (2.68 g) in acetone (35 ml) was added dropwise over 1 hour. The mixture was agitated at the same temperature for 1 hour and at room temperature for 1.5 hours, and then allowed to stand overnight. The precipitated crystals were filtered out. The crystals were washed with ethanol (200 ml), and then dissolved in chloroform (700 ml). The concentration and crystallization were repeated to obtain white crystals (estradiol-3-benzoate) (6.2 g).

An eggplant type flask (300 ml) was charged with the resulting estradiol-3-benzoate (5.6 g), pyridine (1.3 g), and dry tetrahydrofuran (160 ml), and the mixture was agitated under cooling at 0° C. A solution of bromoacetyl bromide (3.5 g) in dry tetrahydrofuran (35 ml) was added dropwise to the mixture over 1 hour. After the end of the addition, the mixture was agitated for further 1.5 hours, and then allowed to stand overnight in a refrigerator (about 5° C.). The precipitated pyridine-HBr salt was filtered out and the filtrate was concentrated to obtain an oily substance (8.4 g). Three components were confirmed by thin layer chromatography [silica gel: cyclohexane/ethyl acetate (5/1; v/v)]. Using silica gel chromatography (developing solvent=the same as in the above thin layer chromatography), compounds having an Rf of 0.71, an Rf of 0.75, and an Rf of 0.87 were obtained in an amount of 1 g, 2.3 g, and 1 g, respectively. The title compound was a compound having an Rf of 0.71.

Rf: 0.71 [cyclohexane/ethyl acetate (5/1; v/v) ]
EI-MS: m/z 512 (parent ion peak)

[4] Preparation of estra-1,3,5(10)-triene-3,17$\beta$-diol-6-one,3-benzoate, 17-monobromoacetate Estradiol (50 g), pyridine (90 g), and dry tetrahydrofuran (400 ml) were placed in a four-neck flask (1 liter). Then, acetic anhydride (94 g) was added thereto and the mixture was refluxed for 6 hours under stirring. The pyridine in the solution was concentrated to about ≠ volume. Then, ethyl acetate (400 ml) and distilled water (300 ml) were added, and the mixture was shaken for extraction. The organic layer was washed two times with equal volumes of distilled water. The organic layer was dried over magnesium sulfate, and then dried under reduced pressure to obtain white crystals (estradiol-3,17$\beta$-diacetate; 64.1 g).

The resulting estradiol - 3,17$\beta$- diacetate (64 g), acetic acid (740 ml), and distilled water (160 ml) were placed in an eggplant type flask (1 liter), and then chromium trioxide (53.8 g) was added portionwise thereto on a bath at 30° to 40° C. After 3 hours, chromium trioxide (6 g) was further added, and then the mixture was agitated at room temperature overnight. The reaction mixture was dispersed in distilled water (3 liters) and extracted with ethyl acetate (1 liter×3). The organic layers were washed with a saturated aqueous solution (1 liter×6) of sodium hydrogen carbonate and distilled water (1 liter×2), dried over magnesium sulfate, and then dried under reduced pressure to obtain a yellow oily substance. The substance was purified by silica gel column chromatography [developing solvent: cyclohexane/ethyl acetate (5/2; v/v)] to obtain white crystals (13.1 g). The compound was confirmed by NMR and IR spectrum to be estradiol-3,17$\beta$-diol-6-one,3,17$\beta$-diacetate.

The resulting estradiol-3,17$\beta$-diol-6-one,3,17$\beta$-diacetate (12 g) and methanol (350 ml) were placed in an eggplant type flask (1 liter). A solution of potassium hydroxide (53 g) in methanol (530 ml) was added to the solution while cooling and the mixture was agitated at room temperature for 2 hours. The mixture was concentrated under reduced pressure to about half of its volume, adjusted to about a pH 4 with 2N-HCl, and then extracted with ethyl acetate (400 ml×3). The organic layers were washed with distilled water (500 ml), dried over magnesium sulfate, and dried under reduced pressure to obtain light yellow crystals (8.74 g). The compound was confirmed by NMR and IR spectrum to be estradiol-3,17$\beta$-diol-6-one.

The resulting estradiol-3,17$\beta$-diol-6-one (2 g) was dissolved in acetone (50 ml) and placed in an eggplant type flask (200 ml). Then, an aqueous solution of NaOH (309 mg) in water (100 ml) and further, a solution of benzoyl chloride (1.04 g) in ethyl ether (10 ml) were added thereto and the mixture was vigorously agitated, whereupon a white substance was quickly precipitated. The white substance was filtered out with a G-4 filter, washed thoroughly with water and dried under reduced pressure to obtain white crystals (2.6 g). The crystals (2 g) and triethylamine (2 g) were dissolved in dry tetrahydrofuran (20 ml). The solution was placed in an Erlenmeyer flask (100 ml), and then agitated under cooling with ice water. Thereafter, a solution of bromoacetyl bromide (4 g) in tetrahydrofuran (20 ml) was added dropwise to the solution, and the mixture was allowed to react under cooling and stirring for 2 hours, and then allowed to stand overnight in a refrigerator (about 5° C.). The resulting precipitate was filtered out with a G-4 filter and the filtrate was dried under reduced pressure to obtain a viscous compound (3.4 g). The viscous compound was purified by silica gel chromatography [developing solvent: cyclohexane/ethyl acetate (5/3; v/v)]. Fractions exhibiting a single spot (Rf=0.63) on thin layer chromatography [silica gel: cyclohexane/ethylene acetate (5/3; v/v)] were collected. The fractions were dried under reduced pressure. The residue was crystallized using a slight amount of ethyl acetate and ethyl ether at −20° C. to obtain white crystals of the title compound (1.7 g)

Rf: 0.63 [cyclohexane/ethyl acetate (5/3; v/v)]

EI-MS: m/z 510 (parent ion peak)

Example 2

Preparation of conjugate

[1] Preparation of 1-methyl-estra-1,3,5(10)-triene-3,17β-diol, 3-benzoate,17-[[4-[4-[bis(2-chloroethyl)amino]phenyl]-1-oxobutoxy]acetate] [=present conjugate (I)]

Chlorambucil (7.2 g), dimethylformamide (100 ml), and 1N-NaOH (26.0 ml) were placed in an eggplant type flask (500 ml). The solvent was removed under reduced pressure at 50° C. with a rotary evaporator and the residue was dried under reduced pressure. Then, the residue was dissolved in dry dimethylformamide (200 ml) again. A solution of the intermediate product obtained in Example 1[1] (9.3 g) in dry dimethylformamide (100 ml) was added thereto. The mixture was agitated at room temperature for 24 hours. After the disappearance of the raw material spot had been confirmed by thin layer chromatography (silica gel), the dimethylformamide was removed under reduced pressure. The residue was dissolved in chloroform (200 ml) and washed once with 200 ml of dilute saline solution. The organic layer was treated with magnesium sulfate and dried under reduced pressure to obtain a light brown oily substance. Further, the residue was purified by silica gel column chromatography [developing solvent: cyclohexane/ethyl acetate (5/1; v/v)] to obtain a colorless oily substance (8.8 g) exhibiting a single spot on thin layer chromatography.

A solution of the colorless oily substance (8.8 g) in ethyl acetate (20 ml) was added portionwise to isopropyl alcohol (1.3 liters), which was agitated on a water bath of 50° C. The mixture was gradually cooled to 0° C. while agitating, and then allowed to stand overnight in a refrigerator at −18° C. The resulting white crystal was filtered out at a low temperature and washed with cold n-hexane (−20° C.). The crystal was dried under reduced pressure at 0° C. for 1 hour and at room temperature for further 4 hours to obtain white crystals (5.2 g) of the present conjugate (I).

Rf: 0.66 [cyclohexane/ethyl acetate (5/2; v/v)]
Elementary analysis for $C_{42}H_{49}Cl_2NO_6$:
  Calculated (%): C:68.65, H:6.72, Cl:9.65, N:1.91
  Found (%): C:68.8, H:6.7, Cl:9.7, N:1.9
EI-MS: m/z 733 (parent ion peak)
$^1$H-NMR (CDCl$_3$): δ
  4.56 ppm (S, CH$_2$, COCH$_2$O)
  3.71–3.60 ppm (m, CH$_2$, N(CH$_2$CH$_2$Cl)$_2$)
  2.23 ppm ( S, CH$_3$, Ar-CH$_3$)
  0.80 ppm (S, CH$_3$, 18-CH$_3$)
Flame reaction: Halogen coloration In the same manner as mentioned above, the present conjugates from (II) to (XI) shown in the following Table 3 were prepared.

TABLE 3

| Conjugate No. | Name of conjugate | Rf[1] | m/z[2] |
|---|---|---|---|
| II | 4-methyl-estra-1,3,5(10)-triene-3,17β-diol,3-benzoate,17-[[4-[4-(bis(2-chloroethyl)amino]phenyl]-1-oxobutoxy]acetate] | 0.65 | 733 |
| III | 2-methyl-estra-1,3,5(10)-triene-3,17β-diol,3-benzoate,17-[[4-[4-[bis(2-chloroethyl)amino]phenyl]-1-oxobutoxy]acetate] | 0.66 | 733 |
| IV | 2-ethyl-estra-1,3,5(10)-triene-3,17β-diol,3-benzoate,17-[[4-[4-[bis(2-chloroethyl)amino]phenyl]-1-oxobutoxy]acetate] | 0.75 | 747 |
| V | 2-isopropyl-estra-1,3,5(10)-triene-3,17β-diol,3-benzoate,17-[[4-[4-[bis(2-chloroethyl)amino]phenyl]-1-oxobutoxy]acetate] | 0.89 | 761 |
| VI | 1,2-dimethyl-estra-1,3,5(10)-triene-3,17β-diol,3-benzoate,17-[[4-[4-[bis(2-chloroethyl)amino]phenyl]-1-oxobutoxy]acetate] | 0.74 | 747 |
| VII | 1,4-dimethyl-estra-1,3,5(10)-triene-3,17β-diol,3-benzoate,17-[[4-[4-[bis(2-chloroethyl)amino]phenyl]-1-oxobutoxy]acetate] | 0.73 | 747 |
| VIII | 2-methoxy-1-methyl-estra-1,3,5(10)-triene-3,17β-diol,3-benzoate,17-[[4-[4-[bis(2-chloroethyl)amimo]-phenyl]-1-oxobutoxy]acetate] | 0.75 | 763 |
| IX | 2-methoxy-estra-1,3,5(10)-triene-3,17β-diol,3-benzoate,17-[[4-[4-[bis(2-chloroethyl)amino]phenyl]-1-oxobutoxy]acetate] | 0.65 | 749 |
| X | 1-methyl-estra-1,3,5(10)-triene-3,17β-diol,3-benzoate,17-[[4-[4-[bis(2-chloroethyl)amino]phenyl]-1-oxobutoxy]-β-propionate] | 0.76 | 747 |
| XI | 1-methyl-estra-1,3,5(10)-triene-3,17β-diol,3-benzoate,17-[[4-[4-[bis(2-chloroethyl)amino]phenyl]-1-oxobutoxy]-γ-butylate] | 0.80 | 761 |

[1]Mobility of silica gel thin layer chromatography Silica gel LK6DF (Whatman Co.) Developing solvent: Cyclohexane/ethyl acetate (5/2; v/v)
[2]Parent ion peak in mass spectrum (EI)

[2] Preparation of 1-methyl-estra-1,3,5(10)-triene-3,17β-diol, 3-(5-dimethylaminonaphthalenesulfonate), 17-[[4-[4-[bis(2-chloroethyl)amino]phenyl]-1-oxobutoxyl]acetate] [=present conjugate (XII)]

Chlorambucil (3.9 g), dimethylformamide (100 ml), and 1N-NaOH (14.1 ml) were placed in an eggplant type flask (500 ml). The mixture was concentrated to about ⅓ volume under reduced pressure at 50° C. with a rotary evaporator. A solution of the intermediate product prepared in Example 1[2] (6.5 g) in dry dimethylformamide (150 ml) was added thereto. The mixture was allowed to react at room temperature for 24 hours and the disappearance of the raw material was confirmed by thin layer chromatography. Then, the dimethylformamide was removed under reduced pressure. Ethyl acetate (150 ml) was added to the residue. The mixture was washed with cool water (100×2 ml). The ethyl acetate layer was dried over magnesium sulfate, and the solvent was removed under reduced pressure to obtain a yellow-brown oily substance. The substance was purified by silica gel chromatography [developing solvent: cyclohexane/ethyl acetate (5/1; v/v)] and a compound exhibiting a single spot by thin layer chromatography (6.2 g) was obtained. The purified product was crystallized from isopropyl alcohol/n-hexane to obtain the present conjugate (XII)(5.1 g).

Rf: 0.52 [cyclohexane/ethyl acetate (5/2; v/v)]
Elementary analysis for $C_{47}H_{56}Cl_2N_2O_7S$:
  Calculated (%): C:63.96, H:6.26, Cl:8.23, N:3.24
  Found (%): C:64.0, H:6.3, Cl:8.2, N:3.2
EI-MS: m/z 862 (parent ion peak)
$^1$H-NMR (CDCl$_3$):δ
  4.59 ppm ( S, CH$_2$, COCH$_2$O)
  3.70–3.59 ppm (m, CH$_2$, N(CH$_2$CH$_2$Cl)$_2$)
  2.90 ppm ( S, CH$_3$, DNS-N(CH$_3$)$_2$)
  2.14 ppm ( S, CH$_3$, Ar-CH$_3$)
  0.70 ppm (S, CH$_3$, E$_2$-18CH$_3$)
Flame reaction: Halogen coloration In the same manner as mentioned above, the present conjugates from (XIII) to (XVI) shown in the following Table 4 were prepared.

TABLE 4

| Conjugate No. | Name of conjugate | Rf | m/z[3] |
|---|---|---|---|
| XIII | 1-methyl-estra-1,3,5(10)-triene-3,17β-diol,3-acetate,17-[[4-[4-[bis(2-chloroethyl)amino]phenyl]-1-oxobutoxy]acetate] | 0.80[1] | 671 |
| XIV | 1-methyl-estra-1,3,5(10)-triene-3,17β-diol,3-palmitate,17-[[4-[4-[bis(2-chloroethyl)amino]phenyl]-1-oxobutoxy]acetate] | 0.63[2] | 867 |
| XV | 1-methyl-estra-1,3,5(10)-triene-3,17β-diol,3-stearate,17-[[4-[4-[bis(2-chloroethyl)amino]phenyl]-1-oxobutoxy]acetate] | 0.75[2] | 895 |
| XVI | 1-methyl-estra-1,3,5(10)-triene-3,17β-diol,3-linolenate,17-[[4-[4-[bis(2-chloroethyl)amino]phenyl]-1-oxobutoxy]acetate] | 0.87[2] | 889 |

[1]Mobility of silica gel thin layer chromatography Silica gel LK6DF (Whatman Co.) Developing solvent: Cyclohexane/ethyl acetate (5/2; v/v)
[2]Mobility of silica gel thin layer chromatography Silica gel LK6DF Developing solvent: Chloroform/ethyl acetate (50/1; v/v)
[3]Parent ion peak in mass spectrum (EI)

[3] Preparation of 1-methyl-estra-1,3,5(10)-triene-3,17β-diol, 3 -palmirate, 17-[[4-[4-[bis(2-chloroethyl)amino]phenyl]-1-oxobutoxy]acetate][ =present conjugate (XIV)]

Pyridine (1.1 g) and 1-methyl-estra-1,3,5(10)-triene-3,17β-diol (2 g) were dissolved in dry tetrahydrofuran (50 ml) and agitated while cooling on an ice-salt bath. A solution of bromoacetyl bromide (2.8 g) in dry tetrahydrofuran (20 ml) was added dropwise thereto. After the addition, the mixture was allowed to react overnight in a refrigerator (about 5° C.). The resulting pyridine-HBr salt was filtered out and the tetrahydrofuran was removed under reduced pressure. The residue was washed with ethanol to obtain 1-methyl-estra-1,3,5(10)-triene-3,17β-diol,3,17-dibromoacetate (3.1 g). The resulting compound was dissolved in acetone (200 ml) and cooled to 0° C. Distilled water was added portionwise thereto to make the condition immediately before precipitation. Then, 1N-NaHCO$_3$ (0.45 ml) was added thereto and the mixture was agitated for 30 minutes. The acetone was removed under reduced pressure, whereupon white crystals were precipitated. The thin layer chromatography showed that the raw material spot remained slightly. The crystals were filtered out, washed, and dried under reduced pressure. The product was purified by silica gel column chromatography [developing solvent: cyclohexane/ethyl acetate (5/1; v/v)] to obtain white crystals (2.5 g). By NMR and elementary analysis, the resulting compound was confirmed to be 1-methyl-estra-1,3,5(10)-triene-3,17β-diol,17-monobromoacetate.

Then, a sodium salt of chlorambucil (1 g) was dispersed in dry tetrahydrofuran (50 ml). A solution of the above-mentioned 1-methyl-estra-1,3,5(10)-triene-3,17β-diol,17-monobromoacetate (1.2 g) in dry tetrahydrofuran (10 ml) was added thereto while being agitated. The mixture was heated at 40° C. for 30 minutes, and then allowed to react at room temperature for further 24 hours. After the disappearance of the raw material had been confirmed by thin layer chromatography, the resulting salt was filtered out and the tetrahydrofuran was removed under reduced pressure to obtain a viscous substance (2.0 g). The product was purified by silica gel column chromatography [developing solvent: cyclohexane/ethyl acetate (5/2; v/v)] to obtain 1-methyl-estra-1,3,5(10)-triene-3,17β-diol,17-[[4-[4-[bis(2-chloroethyl) -amino]phenyl]-1-oxobutoxy]acetate] (1.5 g).

The resulting compound (1.0 g) and dry pyridine (0.25 g) were dissolved in dry tetrahydrofuran (50 ml), and cooled to 0° C. while being agitated. A solution of palmitate chloride (0.87 g) in dry tetrahydrofuran (10 ml) was added dropwise thereto. After the addition, the mixture was agitated at 30° C. for 3 hours, and then allowed to react at room temperature overnight. After the disappearance of the raw material had been confirmed by thin layer chromatography, tetrahydrofuran was removed under reduced pressure. The residue was dissolved again in ethyl acetate (50 ml), washed with water (25 ml×2), then the ethyl acetate layer was dried over anhydrous sodium sulfate and further dried under reduced pressure. The residue was purified by silica gel column chromatography [developing solvent: chloroform/ethyl acetate (50/1 v/v)] to obtain 1.1 g of the present conjugate (XIV).
Rf: 0.63 [chloroform/ethyl acetate ( 50/1; v/v) ]
Elementary analysis for $C_{51}H_{75}O_6Cl_2$:
  Calculated (%): C:70.48, H:8.70, Cl:8.16, N:1.61
  Found (%): C:70.2, H:8.8, Cl:8.2, N:1.6
$^1$H-NMR (CDCl$_3$): δ
  4.57 ppm (S, CH$_2$, COCH$_2$O)
  3.77–3.53 ppm (m, CH$_2$, N(CH$_2$CH$_2$Cl))
  2.17 ppm (S, CH$_3$, Ar-CH$_3$)
  1.5–1.2 ppm (m, CH$_2$, (CH$_2$)$_{14}$)
  0.83 ppm (S, CH$_3$, 18CH$_3$)
EI-MS: m/z : 867 (parent ion peak)
Flame reaction: Halogen coloration In the same manner as above, the present conjugates (XIII), (XV), and (XVI) listed in Table 4 were prepared.

[4] Preparation of estra-1,3,5(10)-triene-3,16α,17β-triol,3-benzoate, 16α-acetate,17-[[4-[4-[bis(2-chloroethyl)amino]phenyl]-1-oxobutoxy]acetate] [=present conjugate (XVII)]

The intermediate compound (1 g) prepared in Example 1 [3]and a potassium salt of chlorambucil (0.65 g) were dissolved in dimethylformamide (80 ml), and reacted while being agitated at room temperature for 24 hours. The reaction solution was concentrated to Δ volume, and ethyl acetate (250 ml) was added to the concentrated solution. The mixture was washed with cold water (150 ml×3), and the organic layer was dried over magnesium sulfate and further dried under reduced pressure to obtain an oily substance (1.9 g). The residue was purified by silica gel column chromatography [developing solvent: cyclohexane/ethyl acetate (5/2; v/v)] and the product was crystallized from isopropanol to obtain a white crystalline precursor (0.6 g), estra-1,3,5(10)-triene-3,16α,17β-triol,3-benzoate, 17-[[4-[4-[bis(2-chloroethyl)amino]phenyl]-1-oxobutoxy]acetate] [precursor of present conjugate (XVII)].
Rf: 0.75 [cyclohexane/ethyl acetate (5/2; v/v)]
Elementary analysis for $C_{41}H_{47}Cl_2NO_7$:
  Calculated (%): C:66.85, H:6.39, Cl:9.65, N:1.90
  Found (%): C:67.0, H:6.5, Cl:9.7, N:1.9
EI-MS: m/z 735 (parent ion peak)
$^1$H-NMR (CDCl$_3$): δ
  4.56 ppm (S, CH$_2$, COCH$_2$O)
  3.70–3.60 ppm (m, CH$_2$, N(CH$_2$CH$_2$Cl)$_2$)
  0.81 ppm (S, CH$_3$, 18-CH$_3$)
Flame reaction: Halogen coloration The precursor (400 rag), dry tetrahydrofuran (15 ml), dry pyridine (1.5 ml), and acetic anhydride (1.5 ml) were placed in an eggplant type flask (50 ml). Then, a condensation tube with a calcium chloride tube was attached to the flask. Thereafter, the mixture was heated and agitated at 60° C. for 6 hours, and then allowed to stand at room temperature overnight. The reaction mixture was dried under reduced pressure and the residue was purified by silica gel column chromatography [developing solvent: cyclohexane/ethyl acetate (5/2; v/v)]. The resulting oily substance (0.6 g) was crystallized from ethyl acetate and isopropanol to obtain white crystals of the present conjugate (XVII) (0.32 g).
Rf: 0.45 [cyclohexane/ethyl acetate (5/2; v/v)]
Elementary analysis for $C_{43}H_{49}Cl_2NO_9$:
  Calculated (%): C:64.99, H:8.94, Cl:8.94, N:1.76
  Found (%): C:65.1, H:9.1, Cl:8.8, N:1.8
EI-MS: m/z 793 (parent ion peak)
$^1$H-NMR (CDCl$_3$): δ
  4.60 ppm ( S, CH$_2$, COCH$_2$O)
  3.71 to 3.60 ppm (m, CH$_2$, N(CH$_2$CH$_2$Cl)$_2$)
  2.0 ppm (S, CH$_3$, COCH$_3$)
  0.83 ppm (S, CH$_3$, 18-CH$_3$)
Flame reaction: Halogen coloration

[5] Preparation of estra-1,3,5(10)-triene-3,17β-diol-6-one,3-benzoate, 17-[[4-[4-[bis(2-chloroethyl)amino]phenyl]-1-oxobutoxy]acetate] [=present conjugate (XVIII)]

Estra-1,3,5(10)-triene-3,17β-diol-6-one,3-benzoate,17-monobromoacetate (500 mg) prepared in Example 1[4] and a potassium salt of chlorambucil (340 mg) were added to dry tetrahydrofuran (20 ml), and agitated at 40° C. for 2 hours. Then, the mixture was allowed to react overnight at room temperature. The resulting potassium salt was filtered out with G-4 filter, and the filtrate was dried under reduced pressure. The residue was purified by silica gel chromatography [developing solvent: cyclohexane/ethyl acetate (50/15; v/v)]. The fractions of a single spot showing Rf=0.24 by a thin layer chromatography with the same developing solvent as above were collected, concentrated under reduced pressure, and crystallized from n-hexane to obtain the present conjugate (XVIII) as white crystals (370 rag).
Rf: 0.24 [cyclohexane/ethyl acetate (50/15; v/v) ]
Elementary analysis for $C_{41}H_{45}Cl_2NO_7$:
  Calculated (%): C:67.03, H:6.13, Cl:9.67, N:1.91
  Found (%): C:66.9, H:6.4, Cl:10.0, N:1.9
EI-MS: m/z 733 (parent ion peak)
$^1$H-NMR (CDCl$_3$): δ
  4.57 ppm ( S, CH$_2$, COCH$_2$O)
  3.70–3.59 ppm (m, CH$_2$, N(CH$_2$CH$_2$Cl)$_2$)
  0.80 ppm (S, CH$_3$, 18-CH$_3$)
Flame reaction: Halogen coloration

Example 3

Toxicity

A suspension of the present conjugate (I) in a 0.5 % methyl cellulose aqueous solution was once orally administered to Wistar rats (male; five weeks old; average weight=130 g; each group consisting of 10 rats) in an amount of 5000 mg/kg, using a metallic stomach tube. Rats were observed for 7 days after administration, but no death was observed. Similar results were observed for the present conjugates from (II) to (XVIII) as well.

Example 4

Estrogen effect (measurement of uterus weight)

Test substances were subcutaneously administered to Wistar/slc rats (female; 3.5 weeks old) for three consecutive days (namely, 50 mg/kg/day, 100 mg/kg/day, and 200 mg/kg/day, respectively). The hormone activity of the present conjugates was compared with that of a comparative substance, by measuring the weights of the uterus on the 4th day. It is to be noted that the above method was described as the excellent method by Koyama (Yoshihiko Koyama, Folia Endocrinologica Japonica, 37(8): 826,1961)

From the relation between the "uterus weight/body weight" ratio on the 4th day and the amount of the substance administered, the amounts of the substances to be administered were calculated that increase the "uterus weight/body weight" ratio to twice the ratio of the control groups. When the present conjugates were administered subcutaneously, sesame oil was used as the solvent. Further, as the comparative substance of conjugate, estra-1,3,5(10)-triene-3,17β-diol,3-benzoate, 17-[[4-[4-[bis(2-chloroethyl)amino)-phenyl]-1-oxobutoxy]acetate](hereinafter referred to as the comparative substance I) was used. The comparative substance I corresponds to the compound of the formula (I) wherein all of $R^1$, $R^3$, $R^4$, and $R^5$ are hydrogen atoms (which is not the present conjugate). Further, estradiol-17β was also used for the comparative test. The results are shown in Table 5.

TABLE 5

| Test substances administered | Number of rats tested | Amount required to increase the "uterus weight/body weight" ratio to twice that of control (mg/kg) |
|---|---|---|
| Present conjugate (I) | 5 × 3 | >200 |
| Present conjugate (II) | 5 × 3 | >200 |
| Present conjugate (III) | 5 × 3 | 25 |
| Present conjugate (IV) | 5 × 3 | 50 |
| Present conjugate (V) | 5 × 3 | 100 |
| Present conjugate (VI) | 5 × 3 | >200 |
| Present conjugate (VII) | 5 × 3 | >200 |
| Present conjugate (VIII) | 5 × 3 | >200 |
| Present conjugate (IX) | 5 × 3 | 100 |
| Present conjugate (X) | 5 × 3 | >200 |
| Present conjugate (XI) | 5 × 3 | >200 |
| Present conjugate (XII) | 5 × 3 | >200 |
| Present conjugate (XIII) | 5 × 3 | >200 |
| Present conjugate (XIV) | 5 × 3 | >200 |
| Present conjugate (XV) | 5 × 3 | >200 |
| Present conjugate (XVI) | 5 × 3 | >200 |
| Present conjugate (XVII) | 5 × 3 | 4.0 |

TABLE 5-continued

| Test substances administered | Number of rats tested | Amount required to increase the "uterus weight/body weight" ratio to twice that of control (mg/kg) |
|---|---|---|
| Present conjugate (XVIII) | 5 × 3 | 1.1 |
| Comparative substance I | 5 × 3 | 0.20 |
| Estradiol-17β | 10 × 3 | 0.02 |

A hormone activity was observed for the comparative substance I in the degree of about 1/10 that of the estradiol-17β. On the other hand, it was observed that the present conjugates carrying a substituent $R^1$ at the 2-position on the ring A of the estradiol and not carrying a substituent on the rings B, C and D exhibited the weakened hormone activity in the degree of 1/100 to 1/500 that of the comparative substance I. No hormone activity was observed for the present conjugate having a substituent at the 1- or 4-position on the ring A or having plural substituents in the above experiments. Further, the hormone activity of the present conjugate not carrying the substituent $R^1$ on the ring A, but carrying substituents on the ring B, C or D, that is, the present conjugates (XVII) and (XVIII), was extremely low, i.e., about 1/20 to 1/5 that of the comparative substance I.

Example 5

Selective antitumor effect (1) Selective growth inhibitory effect for transformed mouse cells (normal mouse cells and transformed cells)

Mouse 3T3 normal cells and transformed cells 3T3SV-40 in the logarithmic growth phase were treated with 0.25 % trypsin. The cells were dispersed in medium (MEM) at $2 \times 10^4$ cells/mi. The cell dispersions were inoculated in test tubes (Ikemoto Rika) in an amount of 1 ml/tube. The tubes were stuffed with cotton and allowed to stationary culture in a carbon dioxide gas incubator (95% air and 5% carbon dioxide gas; constant temperature of 37° C.; humidity of 95%) at an angle of 5° from the horizontal.

The medium was removed after one day elapsed from the inoculation of the cells, and a fresh medium (pH 7.4) was added. Then, each test substance dissolved in dimethyl sulfoxide (10 μg/ml or 50 μg/ml) was added. Whereupon the concentration of the dimethyl sulfoxide was 1 percent with respect to the medium. To a control test tube, only dimethyl sulfoxide was added. The samples were incubated for 5 days after the addition of the test substances. The living cells were counted by counting cells not stained by trypan blue in a Burker-Turk hemocytometer. An average of 3 samples was obtained for each concentration of the test substances. The survival rate (%) was calculated on the basis of the control. The results are shown in Table 6. It was observed that the present conjugates maintained the same activity to selectively inhibit the growth of transformed cells as the comparative substance I.

TABLE 6

| Test substances | Amount administered (μg/ml) | Survival rate of 3T3 (%) | Survival rate of 3T3SC-40 (%) |
|---|---|---|---|
| Present conjugate (I) | 10 | 102 | 55 |
| | 50 | 95 | 14 |
| Present conjugate (II) | 10 | 100 | 50 |
| | 50 | 97 | 19 |
| Present conjugate (III) | 10 | 100 | 54 |
| | 50 | 90 | 15 |
| Present conjugate (IV) | 10 | 100 | 60 |
| | 50 | 90 | 20 |
| Present conjugate (V) | 10 | 103 | 61 |
| | 50 | 89 | 21 |
| Present conjugate (VI) | 10 | 100 | 49 |
| | 50 | 97 | 20 |
| Present conjugate (VII) | 10 | 98 | 53 |
| | 50 | 89 | 10 |
| Present conjugate (VIII) | 10 | 95 | 52 |
| | 50 | 85 | 13 |
| Present conjugate (IX) | 10 | 95 | 50 |
| | 50 | 86 | 15 |
| Present conjugate (X) | 10 | 90 | 60 |
| | 50 | 85 | 11 |
| Present conjugate (XI) | 10 | 85 | 61 |
| | 50 | 75 | 15 |
| Present conjugate (XII) | 10 | 100 | 52 |
| | 50 | 95 | 18 |
| Present conjugate (XIII) | 10 | 75 | 39 |
| | 50 | 69 | 8 |
| Present conjugate (XIV) | 10 | 98 | 53 |
| | 50 | 89 | 10 |
| Present conjugate (XV) | 10 | 100 | 50 |
| | 50 | 92 | 19 |
| Present conjugate (XVI) | 10 | 97 | 58 |
| | 50 | 91 | 24 |
| Present conjugate (XVII) | 10 | 100 | 45 |
| | 50 | 93 | 15 |
| Present conjugate (XVIII) | 10 | 105 | 49 |
| | 50 | 95 | 21 |
| Comparative substance I | 10 | 100 | 50 |
| | 50 | 90 | 15 |
| Chlorambucil | 4.2 | 25 | 20 |
| | 10.5 | 10 | 7 |
| Control | | 100 | 100 |

(2) Selective growth inhibitory effect for human cancer cells (normal human cells and cancer cells)

A growth inhibitory effect (survival rate) of the present conjugates were evaluated for normal human cells (FLOW4000) and various types of human cancer cells [human renal cancer (RC) cells, human prostatic carcinoma (PC-3) cells, and human cervical cancer (HeLa) cells].

Cells subcultured in a culture flask and in the logarithmic growth phase were treated with 0.25% trypsin. The cells were dispersed in medium at $2 \times 10^4$ cells/mi. The cell dispersions were inoculated in test tubes (Ikemoto Rika) in an amount of 1 ml/tube. The tubes were stuffed with cotton and allowed to stationary culture in a carbon dioxide gas incubator (95% air and 5% carbon dioxide gas; constant temperature of 37° C.; humidity of 95%) at an angle of 5° from the horizontal. Each test substance was dissolved in dimethyl sulfoxide and added to the culture systems. The concentration of the dimethyl sulfoxide was 1 percent with respect to the medium.

The medium was removed after one day elapsed from the inoculation of the cells, and a fresh medium containing the test substances and having a pH value listed in Table 7 was added. To a control test tube, only dimethyl sulfoxide was added. The samples were incubated for 5 days after the addition of the test substances. The results were evaluated as in Example 3(1). The survival rate (%) of the present conjugates for the above cells are shown in Table 7. It was observed that the present conjugates maintained the same activity to selectively inhibit the growth of human cancer cells as the comparative substance I.

TABLE 7

| Test substance | Amount added (μg/tube) | Normal cell FLOW 4000 (pH 7.0) | Cancer cells | | |
|---|---|---|---|---|---|
| | | | RC (pH 7.0) | PC-3 (pH 7.0) | HeLa (pH 7.6) |
| Present conjugate (I) | 5 | 101 | 75 | 78 | 50 |
| | 50 | 90 | 24 | 27 | 11 |
| Present conjugate (II) | 5 | 103 | 73 | 82 | 60 |
| | 50 | 94 | 21 | 28 | 10 |
| Present conjugate (III) | 5 | 100 | 79 | 80 | 69 |
| | 50 | 95 | 28 | 32 | 19 |
| Present conjugate (IV) | 5 | 100 | 80 | 78 | 75 |
| | 50 | 98 | 35 | 36 | 25 |
| Present conjugate (V) | 5 | 100 | 85 | 82 | 75 |
| | 50 | 97 | 39 | 38 | 30 |
| Present conjugate (VI) | 5 | 108 | 69 | 85 | 56 |
| | 50 | 90 | 19 | 40 | 22 |
| Present conjugate (VII) | 5 | 100 | 70 | 80 | 59 |
| | 50 | 95 | 25 | 39 | 29 |
| Present conjugate (VIII) | 5 | 100 | 90 | 89 | 90 |
| | 50 | 100 | 40 | 55 | 42 |
| Present conjugate (IX) | 5 | 100 | 73 | 80 | 55 |
| | 50 | 92 | 29 | 30 | 16 |
| Present conjugate (X) | 5 | 95 | 70 | 82 | 60 |
| | 50 | 90 | 25 | 29 | 19 |
| Present conjugate (XI) | 5 | 90 | 70 | 75 | 70 |
| | 50 | 90 | 20 | 35 | 30 |
| Present conjugate (XII) | 5 | 98 | 79 | 80 | 55 |
| | 50 | 92 | 25 | 35 | 20 |
| Present conjugate (VIII) | 5 | 85 | 60 | 65 | 55 |
| | 50 | 75 | 9 | 11 | 8 |
| Present conjugate (XIV) | 5 | 102 | 79 | 85 | 71 |
| | 50 | 95 | 35 | 40 | 30 |
| Present conjugate (XV) | 5 | 100 | 80 | 85 | 75 |
| | 50 | 95 | 35 | 38 | 35 |
| Present conjugate (XVI) | 5 | 102 | 75 | 80 | 73 |
| | 50 | 89 | 30 | 31 | 21 |
| Present conjugate (XVII) | 5 | 100 | 79 | 80 | 51 |
| | 50 | 90 | 25 | 29 | 15 |
| Present conjugate (XVIII) | 5 | 102 | 81 | 84 | 74 |
| | 50 | 89 | 32 | 35 | 32 |
| Comparative substance I | 5 | 92 | 79 | 81 | 52 |
| | 50 | 91 | 23 | 31 | 13 |
| Chlorambucil | 2.1 | 54 | 30 | 39 | 35 |
| | 4.2 | 29 | 29 | 18 | 20 |
| Control | | 100 | 100 | 100 | 100 |

Example 6

Effect for secretion of transforming growth factor from human breast carcinoma cells The effect of the present conjugate (I) on the secretion of transforming growth factor (TGF-α) from a human breast carcinoma cell MCF-7 was examined.

MCF-7 was cultured for 7 days in an MEM medium containing 5% DCC-NBS (dextran-coated charcoal treated newborn bovine serum) and estradiol ($10^{-8}$M) and not containing phenol red. The medium was changed on the 2nd and 4th days. On the 7th day after the cultivation began, the medium was removed and an experimental medium containing 5% DCC-NBS, estradiol ($10^{-8}$M) and a solution of a test substance in dimethyl sulfoxide was added. On the 4th day after the test substance was added, the experimental medium was taken out and centrifuged (3500 rpm for 10 minutes). The supernatant was dialyzed, using a SpectraPot 3 membrane (MW 3500 cut off, Fisher Scientific) against distilled water for 3 days. After the dialysis had been finished, the dialysate was lyophilized to obtain a powder. Then, the powder was dissolved in 1/10 volume of PBS (phosphate-buffered saline) containing 1% bovine serum albumin (BSA).

The TGF-α was measured, using rabbit antibody and mouse monoclonal antibody (ATG-2S) by a sandwich enzyme-linked immunoabsorbent (EIA) method in accordance with Inagaki et al. (Inagaki, H., et. al., J. Immunol. Method., 128: 27–37, 1990). The results are shown in Table 8.

TABLE 8

| Test substances | Protein (mg/dish) | TGF-α secretion (ng/mg-protein) |
|---|---|---|
| Control | 0.62 | 1.32 ± 0.08 |
| $E_2$ $10^{-8}$ M | 0.63 | 2.02 ± 0.09 |
| Present conjugate (I) $10^{-6}$ M + $E_2$ $10^{-8}$ M | 0.59 | 1.20 ± 0.09 |
| Comparative substance I $10^{-6}$ M + $E_2$ $10^{-8}$ M | 0.65 | 1.40 ± 0.10 |
| Chlorambucil $10^{-6}$ M + $E_2$ $10^{-8}$ M | 0.56 | 1.93 ± 0.11 | n = 3, average ± SD

It was observed that the present conjugate (I) completely inhibited, at a concentration of $10^{-6}$M, the production and secretion of TGF-α induced by $10^{-8}$M estradiol ("$E_2$" in the table), in the same manner as the comparative substance I, but an equal molar concentration of chlorambucil did not affect the production and secretion of TGF-α.

Example 7

Antitumor effect (intraperitoneal and oral administration)

A cell suspension prepared by adjusting the number of P388 cells to $1 \times 10^6$ cells/0.05 ml Hanks' solution was intraperitoneally transplanted to a mouse (female; $BDF_1$; 7.5 weeks old). A group for each test consisted of 6 mice, and a control group consisted of 10 mice.

The comparative substance I was dispersed in a physiological saline solution containing 0.5% methyl cellulose. 50 mg/kg or 100 mg/kg of the dispersion was administered intraperitoneally on the 1st, 4th and 7th days after the above transplant of the tumor. Further, the present conjugates were administered in the same manner in an amount (molar ratio) corresponding to 50 mg/kg or 100 mg/kg of the comparative substance I. When administering the present conjugates, a dispersion containing 0.5% methyl cellulose in a physiological saline solution was used if such a dispersion can be prepared. When administering the present conjugates (XIII), (XIV), (XV), and (XVI) which are semisolid at room temperature, the conjugates were dissolved in sesame oil to adjust the concentration thereof so as to correspond an amount of administration of 10 mg/kg and 20 mg/kg of the comparative substance I that was dissolved or dispersed in sesame oil. These preparations were administered orally to P388 tumor-bearing mice for 8 consecutive days. From the number of deaths in each group, the median survival time (MST) was found and referred to as "T" In the same manner, the MST of the control group (group to which only physiological saline solution or sesame oil was administered) was found and referred to as "C" From "T" and "C", T/C × 100 (%) was calculated. The survival checking was ceased on the 45th day from the start of administration of the substances to be tested.

The results of the intraperitoneal administration of the test substances to P388 intraperitoneally transplanted mice are shown in Table 9 and those of the oral administration are shown in Table 10. It was observed in both administrations that the present conjugates exhibit a life-prolonging (macrobiotic) effect comparable or superior to that of the comparative substance I. Further, a life-prolonging effect superior to that of the comparative substance I was observed in the present conjugates (XVII) and (XVIII).

TABLE 9

| Test substance | Dose (mg/kg) | Life-prolonging effect (T/C) × 100% |
|---|---|---|
| Present conjugate (I) | 51 | 288.3 |
| | 102 | >405.4 |
| Present conjugate (II) | 51 | 270.0 |
| | 102 | >405.4 |
| Present conjugate (III) | 51 | 275.0 |
| | 102 | 305.5 |
| Present conjugate (IV) | 52 | 280.0 |
| | 104 | 300.0 |
| Present conjugate (V) | 53 | 250.0 |
| | 106 | 305.5 |
| Present conjugate (VI) | 52 | 278.0 |
| | 104 | >405.4 |
| Present conjugate (VII) | 52 | 260.0 |
| | 104 | 399.0 |
| Present conjugate (VIII) | 53 | 270.3 |
| | 106 | >405.4 |
| Present conjugate (IX) | 52 | 255.0 |
| | 104 | >405.4 |
| Present conjugate (X) | 52 | 200.0 |
| | 104 | 260.0 |
| Present conjugate (XI) | 53 | 205.0 |
| | 106 | 255.0 |
| Present conjugate (XII) | 60 | 261.3 |
| | 120 | 291.0 |
| Present conjugate (XVII) | 55 | 220.0 |
| | 110 | 299.0 |
| Present conjugate (XVIII) | 51 | 215.2 |
| | 102 | 312.1 |
| Comparative substance I | 50 | 145.1 |
| | 100 | 212.7 |

TABLE 10

| Test substance | Dose (mg/kg) | Life-prolonging effect (T/C) × 100% |
|---|---|---|
| Present conjugate (XIII) | 9.3 | 245.0 |
| | 18.6 | 318.2 |
| Present conjugate (XIV) | 12.0 | 256.0 |
| | 24.1 | >405.4 |
| Present conjugate (XV) | 12.4 | 222.0 |
| | 24.9 | >405.4 |
| Present conjugate (XVI) | 12.3 | 225.0 |
| | 24.7 | 380.0 |
| Comparative substance I | 10 | 226.0 |
| | 20 | 289.0 |

Example 8

Antitumor effect (intra-arterial administration of an infection)

Walker 256 carinosarcoma (solid form, about 3 mm × 3 mm × 3 mm) was prepared and subcutaneously transplanted in the left upper arm portion and left thigh portion of Wistar rats (6 weeks old, female; 5 rats a group), by a transplanting needle. On the 8th or 9th day after the transplantation, the test substances were injected (0.1 ml/body) by a catheter from the right femoral artery. The test substances were dissolved or dispersed in Lipiodol (6.5 g) to form injection formulations.

The median survival time (MST) and the life-prolonging rate (T/C) were calculated in the same manner as in Example 7. The results are shown in Table 11. Adriamycin was insoluble in Lipiodol and difficult to retain for a long period in the tumor tissue, and thus did not show the effect sufficiently. The present conjugate (I) was dissolved as sufficiently as the comparative substance I, and exhibited a sustained and sufficient effect.

TABLE 11

| Experiment No. | Test substance | MST (days) | T/C (%) |
|---|---|---|---|
| 1 | Control (physiological saline solution) | 17.5 | — |
| 2 | Lipiodol | 18.5 | 105.7 |
| 3 | Present conjugate (I) (100 mg)[1] | 45.0 | 257.1 |
| 4 | Comparative substance I (100 mg)[1] | 41.0 | 234.3 |
| 5 | Adriamycin (10 mg)[2] | 24.5 | 140.7 |
| 6 | Adriamycin (100 mg)[2] | <1 | <5.7 |

[1] Dissolved in 6.5 g of Lipiodol
[2] Dispersed in 6.5 g of Lipiodol

Example 9

Selective accumulation into cancer tissue transplanted in the liver and estrogen effect by liver intraarterial administration The Walker 256 carcinosarcoma (solid tumor) same as that used in Example 8 was transplanted into the liver of Wistar rats and the reagents from A to E (0.05 ml/body) listed in Tables 12 and 13 were injected into the liver artery. On the 7th day after the injection, the blood sample was collected from each rat, and the amounts of GOT (glutamic oxaloacetic transeuninase) and GPT (gluteunic pyruvic transaminase) were measured. Further, the livers were excised from the rats and the concentrations of the reagents in the tumor and normal tissues in the liver tissue were measured by high performance liquid chromatography. The results are shown in Tables 12 and 13.

TABLE 12

| Formulation (1) | Concentration of test substance in tumor tissue (μg/g wet tissue) (2) | Concentration of test substance in normal tissue (μg/g wet tissue) (3) |
|---|---|---|
| A | N.D. (5) | N.D. (5) |
| B | 13.61 ± 6.21 | 4.30 ± 2.01 |
| C | 12.87 ± 5.17 | 4.78 ± 1.98 |
| D | 6.25 ± 1.89 | 8.94 ± 2.12 |
| E | 7.25 ± 1.69 | 9.83 ± 1.72 |

Average ± SD

TABLE 13

| Formulation (1) | GOT (mU/ml) | GPT (mU/ml) | Ratio of uterus weight (Control = 1) (4) |
|---|---|---|---|
| A | 234 ± 45.0 | 32 ± 2.10 | 0.9 ± 0.2 |
| B | 189 ± 59.84 | 49 ± 8.91 | 0.9 ± 0.1 |
| C | 192 ± 76.74 | 52 ± 9.07 | 1.4 ± 0.2 |
| D | 218 ± 69.21 | 50 ± 7.06 | 1.0 ± 0.2 |

TABLE 13-continued

| Formulation (1) | GOT (mU/ml) | GPT (mU/ml) | Ratio of uterus weight (Control = 1) (4) |
|---|---|---|---|
| E | 227 ± 71.12 | 53 ± 5.69 | 1.5 ± 0.1 |

(1) A: Injection prepared by dissolving 10 mg of adriamycin in 0.5 ml of Urografin, adding 1.5 ml of Lipiodol and emulsifying by ultrasonic waves.
B: Injection prepared by dissolving 10 mg of the present conjugate (I) in 2 ml of Lipiodol.
C: Injection prepared by dissolving comparative substance I (10 mg) in 2 ml of lipiodol.
D: Injection prepared by dissolving 10 mg of the present conjugate (I) in 2 ml of sesame oil.
E: Injection prepared by dissolving 10 mg of comparative substance I (10 mg) in 2 ml of sesame oil.
(2) Concentration of test substance in tumor tissue in liver tissue ($\mu g/g$ wet tissue)
(3) Concentration of test substance in normal liver tissue ($\mu g/g$ wet tissue)
(4) Ratio of the uterus weight of the medicoment-administered group to that of the control group to which only Lipiodol was intra-arterially injected, i.e., the uterus weight of the control group being 1
(5) Not detected
(6) Data is average ± SD When the present conjugate (I) was administered in the form of the Lipiodol injection [Formulation (B)], the concentration thereof in the tumor tissue was higher than that in the normal liver tissue. It was the same result as the Lipiodol injection of the comparative substance I [Formulation (C)]. When the adriamycin injection [Formulation (A)] was used, the remaining reagent was not detected. When the sesame oil injections [Formulations (D) and (E)] were used, no difference was observed between the concentrations of the test substances in the normal liver and those in the tumor tissues. Regarding the influence on uterus weights, a slight uterotrophic effect of the comparative substance I was observed, whereas no uterotrophic effect of the present conjugate was observed.

Example 10

Immunosuppressive effect (1) Heteroantigen stimulating reaction [effect of present conjugate (I) on mitogen reaction]

The present Example examined the effect of the present conjugate (I) on the blastogenesis reaction of lymphocytes responsible to heteroantigen stimulation (measured by the intake of $^3$H-thymidine into cells), that is, the immunoreaction responsible to bacteria or the like. As a mitogen, phytohemagglutinin (PHA) was used because it exhibits the strongest reaction on human lymphocytes (in particular, T cells).

Peripheral venous blood was collected from a healthy male person into a vacuum blood collecting tube and centrifuged (2000 rpm, ordinary temperature, 20 minutes). The serum was further centrifuged (3500 rpm, 4° C., 20 minutes) and the resulting supernatant was added to a medium (RPMI 1640) so that the concentration of the supernatant is 20 percent. The residue obtained by removing the above serum was diluted with the same amount of the same medium as above and the mixture and over a lymphoprep. The whole was centrifuged (1500 rpm, 20° C., 30 minutes). The monocyte layer was taken out and washed twice or three times with the medium, and then the concentration of the cells was adjusted to $5 \times 10^5$ cells/mi.

The resulting cell floating liquid was poured into a 96 well U-bottomed microplate in an amount of 200 $\mu$l/well. The present conjugate (I) and comparative substance I were dissolved respectively in dimethyl sulfoxide and added to the cell floating liquid in an amount of 0.5 percent as a concentration of dimethyl sulfoxide. For a control group, only dimethyl sulfoxide was added. The test was carried out in triplicate for each group. PHA was added to each well in an amount of 10 $\mu$g/ml. After incubation for 2 days in a carbon dioxide gas incubator, $^3$H-thymidine was added in an amount of 1 $\mu$Ci/well. After cultivation for further 18 hours, the cells were harvested on a glass filter with a cell harvester. The radioactivity was measured with a liquid scintillation counter. The results are shown in Table 14. The present conjugate (I) and the comparative substance I did not considerably affect the blastogenesis reaction of lymphocytes responsible to heteroantigen stimulation.

(2) Isoantigen stimulating reaction [effect of present conjugate (I) on mixed lymphocyte culture (MLC)]

The activity of the present conjugate (I) in a mixed lymphocyte culture, a so-called isoantigen stimulating reaction, was investigated as a model of immunoreaction in the transplantation of organ.

Monocytes were obtained from two healthy male persons, respectively, in the same manner as in the above PHA reactions The cells obtained from one of two persons were treated by 15 Gy radiation. After the cells had been washed with the culture medium, the number of the cells was adjusted to $5 \times 10^5$ cells/mi. 100 $\mu$l of each of two types of the cells was poured into each of a same well of a microplate, i.e., 200 $\mu$l as a whole. In the same manner as in the above PHA reactions, the present conjugate (I) and the comparative substance I were dissolved respectively in the dimethyl sulfoxide and added to each well. After incubation for 6 days, $^3$H-thymidine (1 $\mu$Ci/ml) was added. After incubation for further 18 hours, the cells were harvested on a Glass filter with a cell harvester. The radioactivity was measured with a liquid scintillation counter. The results are shown in Table 14. It was observed that the present conjugate (I) inhibited the MLC reaction in the same manner as the comparative substance I.

TABLE 14

| Concentration of test substance ($\mu$g/ml) | Present conjugate (I) | | Comparative substance I | |
|---|---|---|---|---|
| | PHA reaction (%)* | MLC reaction (%)* | PHA reaction (%)* | MLC reaction (%)* |
| 0 (control) | 100 | 100 | 100 | 100 |
| 25 | 65.1 | 5.2 | 59.9 | 7.3 |
| 50 | 90.2 | 6.2 | 87.3 | 10.2 |
| 100 | 85.4 | 5.3 | 75.7 | 7.2 |
| 200 | 70.3 | 2.1 | 66.4 | 7.2 |

*Percentage of intake of $^3$H-thymidine into lymphocytes: relative percentage when the value of the control is 100.

Example 11

GVHR inhibitory effect in bone marrow transplantation model in mouse

The present Example examined the GVHR (graft versus host reaction) inhibitory effect of the present conjugate in a bone marrow transplantation model, using 8-week-old male C3H/He mice and male B6C3F1 mice.

From the spleens of C3H/He mice, spleen cells were obtained by a metal mesh and added to RPMI 1640 containing 10% FBS (fetal bovine serum). From the femur of the same mice, bone marrow cells were washed out using a syringe and added to an RPMI 1640 medium. After each of the floating cells had been washed twice or three times, the concentration of cells was adjusted to $8 \times 10^6$ cells/mi. These were mixed in a ratio of 1:1 and then 0.5 ml of the mixture was injected to B6C3F1 mice in the tail vein. The mice had been pretreated with 9Gy of radiation. Starting from the day before the above transplantation operation, except the day of transplantation, until the 30th day after the transplantation, the present conjugate (I) or the comparative substance I was orally administered each day in an amount of 2 mg/kg in the form of a dispersion in a physiological saline solution containing 0.5% methyl cellulose. To the control group, only 0.5% methyl cellulose physiological saline solution was administered. The survival of the mice was observed. The results are shown in Table 15.

TABLE 15

| Test substance | Amount of oral administration (1) | Number of mice | Median value of survival days after transplantation (2) |
|---|---|---|---|
| Control | 0 | 6 | 8 |
| Present conjugate (I) | 2 | 6 | 30< |
| Comparative substance I | 2 | 6 | 27< |

(1): mg/kg/day.
(2): days

In the control test, the median value of survival days was as low as 8 days, and early deaths believed to be caused by the occurrence of GVHD (graft versus host disease) were observed. On the other hand, in the present conjugate (I), a clear improvement of the survival rate was observed in the mouse bone marrow transplantation model, as in the comparative substance I.

Example 12

Relation to TGF-$\beta$ on inhibitory effect in MLC reactions

To elucidate the mechanism of the selective inhibitory activity of the present conjugate (I) on the MLC reaction, a solution was prepared by dissolving TGF-$\beta$ (R&D Systems) and anti-TGF-$\beta$ antibodies (R&D Systems) in RPMI 1640, and added under the same experimental conditions as in Example 10(2). The results are shown in Table 16.

TABLE 16

| | MLC reaction (%) (1) | |
|---|---|---|
| Test substance | Present conjugate (I) | Comparative substance I |
| Control | 100 ± 13 | 100 ± 13 |
| TGF-$\beta$ (10 ng/ml) | 44 ± 26 | 44 ± 26 |
| Anti-TGF-$\beta$ antibody (10 ng/ml) | 93 ± 22 | 93 ± 22 |
| Conjugates 20 $\mu$g/ml (2) | 46 ± 18 | 34 ± 22 |
| Conjugates + TGF-$\beta$ (2) | 16 ± 14 | 7 ± 7 |
| Conjugates + anti-TGF-$\beta$ antibody (2) | 83 ± 13 | 97 ± 29 |

(1) Percentage of intake of $^3$H-thymidine into lymphocytes: Control = 100. n = 3, average ± SD.
(2) The "conjugates" indicates the present conjugate or the comparative substance.

It was observed that the present conjugate exhibited the inhibition of the MLC reaction comparable to that by the immunosuppressive substance (TGF-$\beta$), and further a combined effect with the TGF-$\beta$. The anti-TGF-$\beta$ antibody did not affect the MLC reaction. The combination of the present conjugate (I) and the anti-TGF-$\beta$ antibody substantially neutralized the inhibitory activity of the MLC reaction obtained by the single use of the present conjugate (I). The above behavior of the present conjugate is similar to that of the comparative substance I. Therefore, it is considered that mechanism of inhibitory effect by the present conjugate relates to TGF-$\beta$ in the MLC reaction.

Formulation Example 1: Tablet

| Present conjugate (I) | 30 parts |
|---|---|
| Mannitol | 35 parts |
| Sorbitol | 25 parts |
| Carboxymethylcellulose | 5 parts |
| Magnesium stearate | 5 parts |
| Talc | 40 parts |

The above components were thoroughly mixed and the mixture was compressed to form tablets of a diameter of 10 mm.

Formulation Example 2: Injection

The present conjugate (I) (100 rag) was added to Lipiodol (6.5 g) at 25° C. and the mixture was stirred for 15 minutes to obtain a solution as an injection of the present conjugate (I). The solution was filled in sterilized vials.

Formulation Example 3: Capsule

The mixture prepared in Formulation Example 1 was inserted and sealed in a No. 0 capsule to obtain a capsule.

Formulation Example 4: External Agent

The present conjugate (I) (1 g), sesame oil (10 g), white vaseline (90 g), and N,N-diethanol lauramide (penetration enhancer: 10 g) were heated to melt on a water bath and mixed. The mixture was cooled to room temperature to obtain an external agent.

Formulation Example 5: Suppository

The present conjugate (I) (100 mg), sesame oil (5 g), and Witepsol (90 g) were heated to melt and mixed on a water bath. 1.33 g of the melted mixture was filled in a plastic suppository container and cooled to room temperature to obtain a suppository.

Although the present invention has been described with reference to specific examples, various changes and modifications obvious to those skilled in the art are deemed to be within the spirit, scope, and concept of the invention.

We claim:

1. An estradiol derivative-chlorambucil conjugate of the formula ( I ):

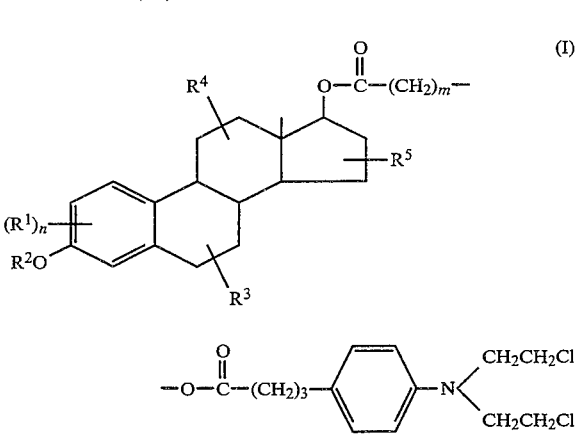

wherein $R^1$ is alkyl or alkoxyl of 1 to 4 carbon atoms; $R^2$ is acyl, dansyl, or alkyl; $R^3$, $R^4$, and $R^5$ independently are H, oxo, OH, or acyloxy; m is an integer of 1 to 3; and n is an integer of 0 to 3; provided that when n is 0, all of $R^3$, $R^4$, and $R^5$ are not H at the same time, and at least one of $R^3$, $R^4$, and $R^5$ is a group other than H and OH; and further, that when n is 2 or 3, the groups $R^1$ are the same or different.

2. A conjugate according to claim 1, wherein the oxygen atom at the 17-position of the estradiol derivative is in configuration.

3. A conjugate according to claim 1, wherein $R^2$ is acyl and is selected from the group consisting of benzoyl, acetyl, palmitoyl, stearoyl and linolenoyl.

4. A conjugate according to claim 1, wherein $R^2$ is alkyl and is alkyl of 1 to 4 carbon atoms.

5. A conjugate according to claim 1, wherein $R^3$, $R^4$, or $R^5$ is acyloxy and is selected from the group consisting of benzoyloxy, acetoxy, propanoyloxy, butanoyloxy, and pentanoyloxy.

6. A pharmaceutical composition comprising an estradiol derivative-chlorambucil conjugate of the formula (I):

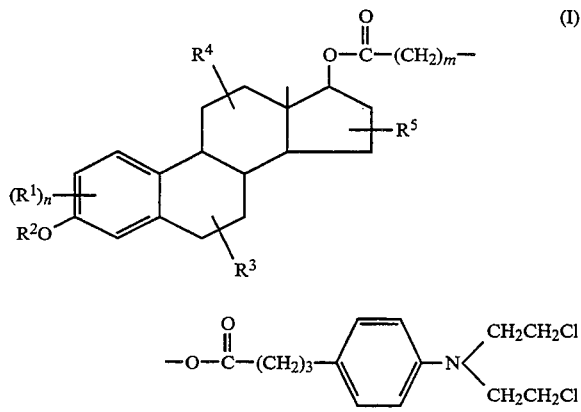

wherein $R^1$ is alkyl or alkoxyl of 1 to 4 carbon atoms; $R^2$ is acyl, dansyl, or alkyl; $R^3$, $R^4$, and $R^5$ independently are H, oxo, OH, or acyloxy; m is an integer of 1 to 3; and n is an integer of 0 to 3; provided that when n is 0, all of $R^3$, $R^4$, and $R^5$ are not H at the same time, and at least one of $R^3$, $R^4$, and $R^5$ is a group other than H and OH; and further, when n is 2 or 3, the groups $R^1$ are the same or different, and a pharmaceutically acceptable carrier.

7. A composition according to claim 6, in the form of an injection.

8. An injectable composition according to claim 7 comprising the estradiol derivative-chlorambucil conjugate according to claim 6 dissolved in an ester of iodinated poppy oil fatty acid.

9. A composition according to claim 6, in the form of a capsule agent.

10. A composition according to claim 6, in the form of a tablet.

11. A composition according to claim 6, in the form of a suppository.

12. A composition according to claim 6, in the form of an external agent.

* * * * *

UNITED STATES PATENT AND TRADEMARK OFFICE
CERTIFICATE OF CORRECTION

PATENT NO. : 5,354,745
DATED : October 11, 1994
INVENTOR(S) : FUMIO TAMURA, TSUYOSHI SAITO, SATOSHI MITSUHASHI, TADAHIRO MATSUDAIRA, KIRO ASANO It is certified that error appears in the above-indentified patent and that said Letters Patent is hereby corrected as shown below:

In column 3, line 68, delete "(5-dimethyleuninonaph-" and insert -- (5-dimethylaminonaph- --.

In column 5, line 55, delete "OH" and insert -- OH --.

In column 8, line 46, delete "(layer thickness=250 ram" and insert -- (layer thickness=250 mm --.

In column 11, line 64, delete "$\neq$" and insert -- ½ --.

In column 16, line 63, delete "$\Delta$" and insert -- ½ --.

In column 17, line 18, delete "(400 rag)" and insert -- (400 mg) --.

In column 21, Table 7, first column, delete "(VIII)" (second occurrence) and insert -- (XIII) --.

In column 23, line 56, delete "infection)" and insert -- injection) --.

In column 25, Table 13, footnote (4), delete "medicoment" and insert -- medicament --.

UNITED STATES PATENT AND TRADEMARK OFFICE
CERTIFICATE OF CORRECTION

PATENT NO. : 5,354,745

DATED : October 11, 1994

INVENTOR(S) : FUMIO TAMURA, TSUYOSHI SAITO, SATOSHI MITSUHASHI, TADAHIRO MATSUDAIRA, KIRO ASANO

It is certified that error appears in the above-indentified patent and that said Letters Patent is hereby corrected as shown below:

In column 25, line 61, delete "cells/mi" and insert -- cells/ml --.

In column 26, line 24, delete "cells/mi" and insert -- cells/ml --.

In column 29, Claim 2, line 3, before "configuration" insert -- $\beta$- --.

Signed and Sealed this

Twenty-first Day of February, 1995

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,354,745

DATED : October 11, 1994

INVENTOR(S) : Fumio Tamura, et al

It is certified that error appears in the above-identified patent and that said Letters Patent is hereby corrected as shown below:

Column 8, line 46, change "(layer thickness=250 ram " to --layer thickness=250 $\mu$m --.

Signed and Sealed this

Twenty-eighth Day of November 1995

Attest:

BRUCE LEHMAN

Attesting Officer    Commissioner of Patents and Trademarks